US010080636B2

United States Patent
Thiel et al.

(10) Patent No.: US 10,080,636 B2
(45) Date of Patent: Sep. 25, 2018

(54) METHOD FOR MEASURING A DENTAL SITUATION

(71) Applicant: Sirona Dental Systems GmbH, Bensheim (DE)

(72) Inventors: Frank Thiel, Ober-Ramstadt (DE); Sascha Schneider, Muhltal (DE)

(73) Assignee: Sirona Dental Systems GMBH, Bensheim (DE)

( * ) Notice: Subject to any disclaimer, the term of this patent is extended or adjusted under 35 U.S.C. 154(b) by 558 days.

(21) Appl. No.: 14/399,271

(22) PCT Filed: May 7, 2013

(86) PCT No.: PCT/EP2013/059426
§ 371 (c)(1),
(2) Date: Nov. 6, 2014

(87) PCT Pub. No.: WO2013/167555
PCT Pub. Date: Nov. 14, 2013

(65) Prior Publication Data
US 2015/0072313 A1  Mar. 12, 2015

(30) Foreign Application Priority Data
May 7, 2012 (DE) .................. 10 2012 207 499

(51) Int. Cl.
*A61C 19/04* (2006.01)
*A61C 9/00* (2006.01)
*A61B 6/14* (2006.01)

(52) U.S. Cl.
CPC ............ *A61C 19/04* (2013.01); *A61B 6/14* (2013.01); *A61C 9/006* (2013.01); *A61C 9/008* (2013.01); *A61C 9/0046* (2013.01); *A61C 9/0073* (2013.01)

(58) Field of Classification Search
CPC .......... A61C 1/007; A61C 3/02; A61C 9/006; A61C 9/004; A61C 9/0053; A61C 9/0046; A61C 9/0073; A61C 9/008; A61B 6/14
(Continued)

(56) References Cited

U.S. PATENT DOCUMENTS 4,837,732 A * 6/1989 Brandestini ........ A61C 13/0004
356/604
5,372,502 A * 12/1994 Massen .................. G01B 11/24
433/215
(Continued)

FOREIGN PATENT DOCUMENTS

DE 10 2004 035 090 A1 2/2006
DE 10 2004 035 091 A1 2/2006
(Continued)

OTHER PUBLICATIONS

German Office Action dated Dec. 20, 2012, issued in corresponding German Patent Application No. 10 2012 207 499.6.
(Continued)

*Primary Examiner* — Nicholas Lucchesi
(74) *Attorney, Agent, or Firm* — Fitzpatrick, Cella, Harper & Scinto

(57) ABSTRACT

The invention relates to a method for measuring a dental situation comprising a plurality of implants and/or preparations for inserting dental restorations. Using a first measuring method, a first region of the dental situation is initially recorded while first measurement data are generated. The first region is selected to comprise at least two implants and/or preparations. Subsequently, object regions surrounding the implants and/or the preparations are established, and, while using a second measuring method, the established object regions are detected, and second measurement data (Continued)

are generated. The second measuring method is more precise than the first measuring method.

19 Claims, 2 Drawing Sheets

(58) Field of Classification Search
USPC .................... 433/24, 27, 29, 215; 348/77
See application file for complete search history.

(56) References Cited

U.S. PATENT DOCUMENTS

| | | | |
|---|---|---|---|
| 5,448,472 A * | 9/1995 | Mushabac | A61C 13/0004 433/70 |
| 6,287,121 B1 | 9/2001 | Guiot et al. | |
| 7,234,937 B2 | 6/2007 | Sachdeva et al. | |
| 7,259,871 B2 | 8/2007 | Chen | |
| 7,623,693 B2 | 11/2009 | Holzner et al. | |
| 7,840,042 B2 | 11/2010 | Kriveshko et al. | |
| 7,978,892 B2 | 7/2011 | Quadling et al. | |
| 8,334,894 B2 | 12/2012 | Pfeiffer et al. | |
| 8,615,128 B2 | 12/2013 | Schwotzer et al. | |
| 9,314,150 B2 * | 4/2016 | Chen | A61B 1/247 |
| 2006/0019219 A1 | 1/2006 | Saliger et al. | |
| 2006/0263742 A1 | 11/2006 | Saliger | |
| 2007/0046663 A1 | 3/2007 | Brinkmann et al. | |
| 2007/0248929 A1 | 10/2007 | Holzner et al. | |
| 2008/0038688 A1 | 2/2008 | Kopelman et al. | |
| 2009/0279103 A1 * | 11/2009 | Thiel | A61B 5/0088 356/608 |
| 2010/0046005 A1 | 2/2010 | Kalkowski et al. | |
| 2010/0296710 A1 | 11/2010 | Schneider et al. | |
| 2010/0311005 A1 * | 12/2010 | Liang | A61B 1/00009 433/29 |
| 2011/0136080 A1 | 6/2011 | Holzner et al. | |
| 2011/0287387 A1 * | 11/2011 | Chen | A61C 9/006 433/215 |
| 2012/0075425 A1 | 3/2012 | Thiel | |
| 2012/0224756 A1 | 9/2012 | Ertl | |
| 2014/0104406 A1 * | 4/2014 | Pfeiffer | G06T 11/60 348/77 |
| 2014/0146142 A1 | 5/2014 | Duret et al. | |
| 2014/0253686 A1 * | 9/2014 | Wong | H04N 13/0285 348/46 |

FOREIGN PATENT DOCUMENTS

| | | |
|---|---|---|
| DE | 10 2004 051 165 B3 | 6/2006 |
| DE | 10 2007 005 726 A1 | 8/2008 |
| DE | 10 2007 056 820 A1 | 6/2009 |
| DE | 10 2008 006 048 A1 | 7/2009 |
| DE | 10 2009 001 086 A1 | 9/2010 |
| DE | 10 2009 038 588 A1 | 3/2011 |
| DE | 10 2008 055 158 B4 | 12/2011 |
| DE | 10 2008 054 985 B4 | 2/2012 |
| EP | 0913130 A2 | 5/1999 |
| EP | 1820469 A1 | 8/2007 |
| EP | 1 757 902 B1 | 11/2007 |
| EP | 2 110 098 A1 | 10/2009 |
| FR | 2977469 A1 | 1/2013 |
| WO | 94/00074 A1 | 1/1994 |
| WO | 9400074 A1 | 1/1994 |
| WO | 2008/046663 A2 | 4/2008 |
| WO | 2008/051130 A1 | 5/2008 |
| WO | 2008/083857 A1 | 7/2008 |
| WO | 2012/007003 A1 | 1/2012 |
| WO | 2013/008097 A1 | 1/2013 |

OTHER PUBLICATIONS

Opposition filed by 3M Innovative Properties Company, Dec. 4, 2013.
Intraoraler 3D-Digitalisierer fur CAD/CAM in the Zahnmedizin, Fraunhofer IOF Annual Report 2007, pp. 116-117.
V.A. Knyaz et al., Photogrammetric Techniques for Dentistry Analysis, Planning and Visualisation, State Research Institute of Avaition Systems, pp. 783-788.
Opposition filed by DeguDent GmbH, Dec. 5, 2013.
Framework Management Digital, Amann Girrbach AG, pp. 1-44.
Torsten Jemt et al., Photogrammetry—An Alternative to Conventional Impressions in Implant Dentistry A Clinical Pilot Study, The International Journal of Prosthodontics, vol. 12, No. 4, 1999, pp. 363-368.
Sirona Dental Systems GmbH Operators Manual, Optical Impression, Jan. 2010, pp. 75-100.
International Search Report dated Jul. 31, 2013, in PCT Application No. PCT/EP2013/059426.
International Preliminary Report on Patentability dated May 9, 2014 in PCT Application No. PCT/EP2013/059426.

* cited by examiner

METHOD FOR MEASURING A DENTAL SITUATION

CROSS-REFERENCE TO RELATED APPLICATIONS

This application is a national stage entry of PCT/EP2013/059426 which was filed on May 7, 2013, and which claims priority to German Patent Appln. No. 10 2012 207 499.6 filed May 7, 2012.

FIELD OF INVENTION

The invention relates to a method for measuring a dental situation. The dental situation includes a plurality of implants and/or preparations for inserting dental restorations. Initially, a first region of the dental situation is detected using a first measuring method. First measurement data are generated thereby. The first region comprises at least two implants and/or preparations.

BACKGROUND OF THE INVENTION

Several methods for measuring dental situations are known from the prior art in which the relative position of implants or preparations to each other is determined.

Typically, implant positions and implant orientations are measured using a conventional impression, and a plaster model is created. The plaster model is then measured, and the positions and orientations of the implants are determined using the generated measurement data. In this method, generally the relative position and orientation of the implants to each other and relative to the remaining teeth are determined.

In an alternative method, the dental situation can be measured using an optical, three-dimensional measuring method in order to subsequently digitally determine the position and orientation of the implants relative to each other and relative to the residual dentition.

DE 10 2004 035 091 A1 discloses a method for determining the position and orientation of a dental implant as well as a top part. Measurement geometry is superimposed on the implant, which permits an inference of the position and orientation of the implant. This is followed by a three-dimensional measurement of the dental situation, during which measurement data are generated. Within the measurement data, the measured body is identified, and the position and orientation of the measured body are determined. Then the position and orientation of the implant are determined using the position and orientation of the measurement geometry. Various embodiments of the top part are disclosed which for example can be designed in the form of a hexagon.

DE 10 2004 035 090 A1 discloses a compensating part and a method for the measurement of dental restorations. A top part is placed on a manipulated implant provided in a working model, the top part comprising contact surfaces for contacting the gingiva surrounding the dental restoration. The top part can have an ID which makes it possible to determine the orientation of the top part.

DE 10 2007 056 820 A1 discloses a measuring body for an implant, and a method to determine a 3D measured image. The measuring body has a measurement geometry which is detected by means of a measuring camera. The alignment and orientation of the implant can then be determined using the measurement geometry.

A disadvantage of the aforementioned method is that the quality of the images for determining the position and orientation of the implants relative to each other is frequently insufficient. At the same time, an image with a greater resolution is frequently impossible due to the associated longer imaging time.

The object of the following invention is therefore to provide a method for measuring a dental situation which enables precise determination of the position and orientation of implants relative to each other.

SUMMARY OF THE INVENTION

In one embodiment, a method to measure a dental situation comprising a plurality of implants and/or preparations for inserting dental restorations, wherein when a first measuring method is used, a first region of the dental situation is recorded while initial measurement data are generated, the first region comprising at least two implants and/or preparations, characterized in that object regions are established around the implants and/or the preparations and, while using a second measuring method, the established object regions are detected while second measuring data are generated, the second measuring method being more precise than the first measuring method.

BRIEF DESCRIPTION OF THE DRAWINGS

The invention will be explained with reference to the drawings. In the figures.

DETAILED DESCRIPTION OF THE INVENTION

Figure 1:
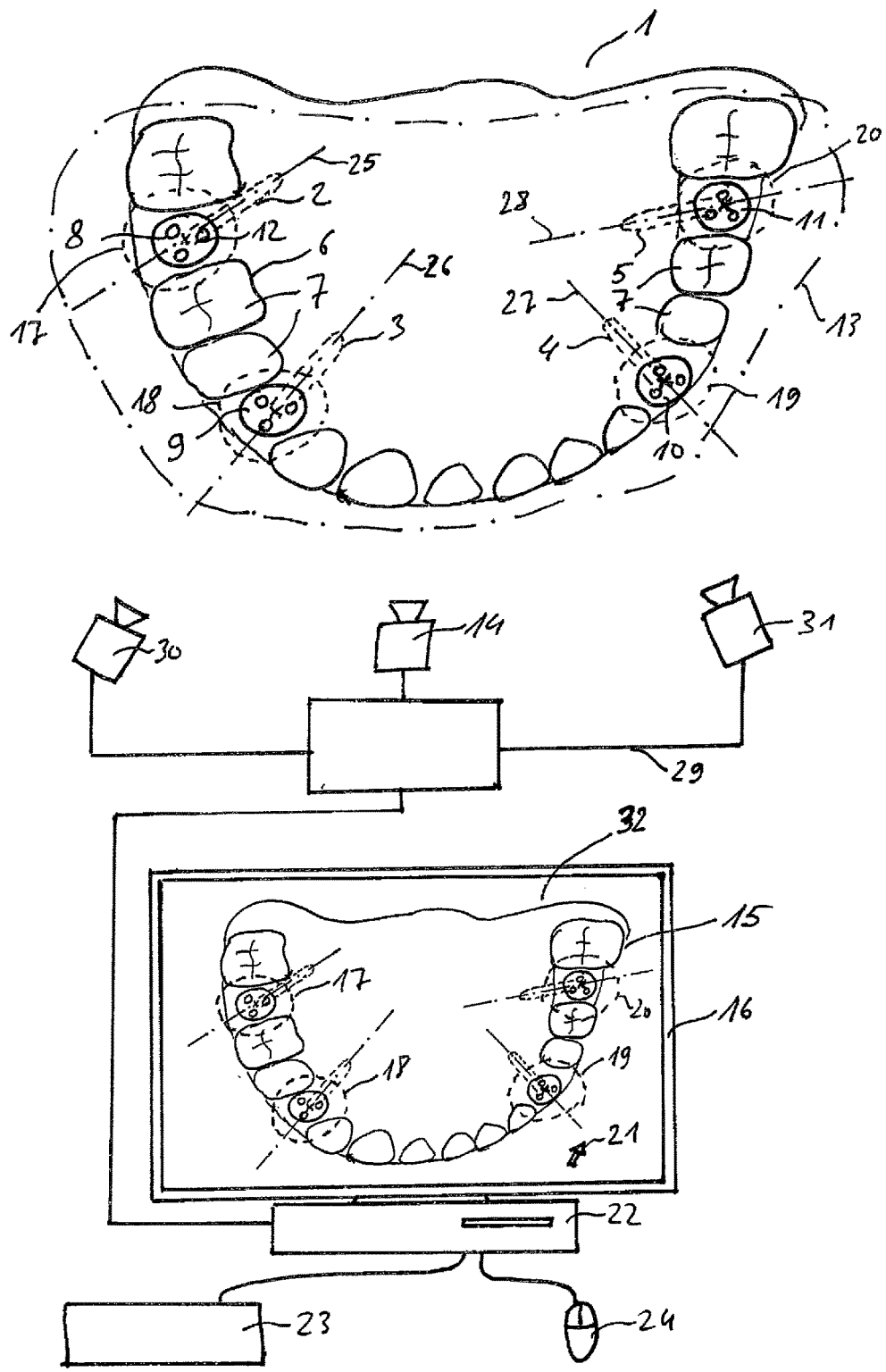
FIG. 1 shows a sketch of the dental situation to illustrate the method.

The invention relates to a method for measuring a dental situation comprising a plurality of implants and/or preparations for inserting dental restorations. Initially, a first region of the dental situation is detected using a first measuring method. First measurement data are generated thereby. The first region comprises at least two implants and/or preparations. Then object regions are established around the implants and/or the preparations and, using a second measuring method, the established object regions are detected. Second measurement data are thereby generated, and the second measuring method is more precise than the first measuring method.

The method for measuring the dental situation can be applied both to a dental situation in the oral cavity of the patient, as well as to a dental model of the dental situation. The dental model can for example be created by means of a plaster impression of the dental situation. The implants can be designed as desired and possess a specific connecting geometry for an abutment to be inserted, or an appropriate dental restoration. To improve the measurement, measuring bodies can be used which are connected to the implants. The measuring bodies can have specific measurement geometries which enable the position and orientation of the implants to be determined. The measurement geometry can have a specific geometric shape such as a polygon, or for example three points arranged in a triangle. The measuring bodies can be designed to be suitable for measurement using the first measuring method and the second measuring method. When measuring using an x-ray imaging method, the measuring bodies can for example be sensitive to x-rays. The present method can also be used to measure preparations. The first region can comprise a part of the dental situation with at least two implants, or the entire dental situation. The generated first measurement data can be three-dimensional image data, or raw data for later processing. The object regions can be shaped in any manner; for example, they can have a circular shape around the implants. The second measurement data can be three-dimensional image data, or raw data for further processing. The second measurement data are more precise, for example in terms of the resolution and precision, in comparison to the first measurement data. The deviation of the second measurement data from the actual dimensions of the imaged object is therefore less than is the case with the first measurement data.

An advantage of this method is that an overview image can be first generated by means of the first measuring method, and then a more precise image can be generated by means of the second measuring method. This makes it possible to more precisely measure the implants to determine the position and orientation of the implants relative to each other and relative to the dental situation, the duration of measurements being shortened.

The first measurement data and the second measurement data can be advantageously combined into a superimposed image of the dental situation.

The first measurement data and the second measurement data in the superimposed image can be combined by means of a pattern recognition algorithm which identifies matching regions. The superimposed image enables a quick overview for the user of the entire dental situation with the integrated, more precise second measurement data of the object regions around the implants.

The object regions can be advantageously established manually by a user.

When manually establishing the object regions, the user can use a computer to form a border around the object regions with a mouse cursor. The user can also use a virtual tool, a center point of a circular object region being first established on an axis of symmetry of an implant, and then a circle being drawn around this point at an appropriate distance.

The object regions can be advantageously established automatically by means of a search algorithm.

When the object regions are automatically established, the implants can be recognized using the search algorithm assisted by a computer. Subsequently, a circular object region around each of the recognized implants can be automatically established at a specific distance from the axis of symmetry of the implant. The distance to the center point can for example be 2 mm to 10 mm.

Advantageously, the first measuring method can be based on a fringe projection method, a confocal microscopy method, a white light interferometry method, a triangulation method with colored patterns, or a three-dimensional x-ray imaging method.

With the known fringe projection method, the measured object is illuminated with a strip pattern consisting of parallel light and dark strips of different widths. In a further step, the projected strip pattern is recorded by means of a camera at a known viewing angle relative to the projection. Using a so-called phase shift method, a projection coordinate can be determined which indicates the number of the strip. The number of the strip in the projector corresponds to an image coordinate in the camera. At a known camera position and known projector position relative to the object, an intersection can be calculated between a plane which is defined by the respective strip, and a straight line which is defined by the coordinate in the camera. The three-dimensional coordinates of the surface are determined in this manner for each of the measuring points.

In white light interferometry, a light with a short coherence length is used, so that colored indifferences arise when the path lengths within the reference and object beam are nearly equal. When the path lengths change, the interference pattern changes so that the distance to the surface of the measured object can be determined by means of the interference pattern.

In three-dimensional confocal microscopy, the surface of the digital object is scanned in steps during which a focal plane is moved in steps. The light outside of the focal plane is suppressed as much as possible by means of a pinhole diaphragm. Subsequently, a three-dimensional model of the measured object can be calculated from the measured image data from the individual steps of different focal planes.

In the triangulation method with colored patterns, several light sources of different colors, or one light source with several filters of different colors, and a projection grid can be used to generate the projected colored pattern. Colored patterns can be generated thereby which are clearly delineated from each other, such as parallel lines of different colors, which are projected on the dental object. This method can be used as the first measuring method to generate the first measurement data, and/or as the second measurement method to generate the second measurement data.

The three-dimensional x-ray imaging method can for example be a DVT or CT method. The first measuring method or the second measuring method can also be an MRT method.

Advantageously, the second, more precise measuring method can also be based on a triangulation method and on a fringe projection method in which at least the object regions to be imaged are powdered beforehand.

For a precise image, a non-reflective surface of the object to be measured is absolutely essential. To accomplish this, the digital object is generally coated with a special powder before imaging. After imaging, the applied powder coating is removed. Without powdering, only limited accuracy is achieved since imaging errors are generated by uneven reflections.

Advantageously, the second, more precise measuring method can be based on a triangulation method in which a second triangulation angle can be less than a first triangulation angle of the first measuring method and is selected to be small enough to satisfy the precision requirements of the second measurement data.

The second triangulation angle of the second, more precise measuring method is chosen to be small enough to satisfy the precision requirements such as a sufficient resolution.

Advantageously, the second, more precise measuring method can be performed by means of a multi-camera system and be based on a photogrammetry method.

The photogrammetry method is a measuring method and evaluation method for remote sensing in order to determine, from images and precise measuring pictures of an object, the spatial position or three-dimensional shape thereof. Generally, the pictures are taken with a special multi-camera system. By means of this method, a three-dimensional image of the object to be imaged can be calculated from the two-dimensional optical images from the individual cameras of the multi-camera system.

Advantageously, the second, more precise measuring method can be performed by means of a tactile scanner by scanning points of the object regions.

The tactile scanner can be a device which scans the object regions point for point and generates a depth coordinates for each object point. A three-dimensional surface of the object to be measured can be generated from the detected depth coordinates.

Advantageously, the second, more precise measuring method can be based on a three-dimensional x-ray imaging method with a greater resolution than in the first measuring method.

In a DVT or CT method, the resolution of the generated three-dimensional x-ray picture can be achieved by reducing the slice sequence, which is associated with an increased exposure.

Advantageously, the position and orientation of the implants and/or the preparations can be determined relative to each other and relative to the teeth by means of the second measuring data of the established object regions.

To improve the measurement, measuring bodies can be placed on the implants which facilitate determination of the position and orientation of the implants. The measuring bodies or the visible regions of the inserted implants can for example be identified in the second measuring data by means of a computer algorithm, wherein the position and orientation of the implants relative to each other and relative to the teeth can subsequently also be determined automatically by means of a computer algorithm.

Advantageously, the second, more precise measuring method can be performed by means of a multi-camera system and can be based on a photogrammetry method in which the object regions in each of the individual images from the multi-camera system can be established. Subsequently, a three-dimensional image of the object regions can be reconstructed by means of a computer algorithm using the second measurement data of the object regions from the individual images.

Consequently, only the object regions are used for the reconstruction of the three-dimensional image. This eventuates in a shorter computing time in the reconstruction of the three-dimensional image.

Example

FIG. 1 shows a sketch to illustrate the method for measuring a dental situation 1 comprising a plurality of implants 2, 3, 4 and 5 for insertion of dental restorations. A residual dentition 6 comprises a plurality of neighboring teeth 7. The first implant 2 is connected to a first measured body 8, the second implant 3 is connected to a second measured body 9, the third implant 4 is connected to a third measured body 10, and the fourth implant 5 is connected to a fourth measured body 11. The measuring bodies 8, 9, 10 and 11 have a measurement geometry 12 consisting of three points that enable the determination of the position and orientation of the implants 2, 3, 4 and 5 relative to the teeth 7 and relative to each other. In the first method step, a first region 13 which is depicted by a dot-dashed line is measured by means of a camera 14 using a first measuring method. An overview image of the entire dental situation 1 is generated thereby. The first measuring method can for example be based on a fringe projection method, a confocal microscopy method, a white light interferometry method, a triangulation method with colored patterns, or on a three-dimensional x-ray imaging method. The overview image 15 is displayed by means of a display device 16 such as a monitor. Subsequently in the next method steps, the object regions 17, 18, 19 and 20 around the implants 2, 3, 4 and 5 are established. The object regions can either be established manually by the user using a mouse cursor 21, or automatically. To further process the picture, a computer 22 is used with means of input such as a keyboard 23 and a mouse 24. The object regions 17, 18, 19 and 20 are depicted by a dashed line and are formed circular with a center point which coincides with an axis of symmetry 25, 26, 27 and 28 of the implants 2, 3, 4 and 5. Subsequently, the established object regions 17, 18, 19 and are detected by means of a multi-camera system 29 consisting of a first camera 30 and a second camera 31. Second measured data are thereby generated which are more precise than the first measured data of the overview image 15. The second measured data have a higher resolution than the first measured data and hence permit a more precise determination of the position and orientation of the implants 2, 3, 4 and 5. Subsequently, the first measured data of the overview image 15 and second measured data of the established object regions are combined into a superimposed image 32 which is depicted by means of the display device 16. Consequently, the user can quickly become oriented and determine the position and orientation of the implants 2, 3, 4 and 5 using the object regions 17, 18, 19 and 20. The position and orientation of the implants 2, 3, 4 and 5 can also be determined automatically by means of a computer algorithm in which the measuring bodies 8, 9, 10 and 11 are targeted. The outcome of this method is accordingly the precise position and orientation of the implants 2, 3, 4 and 5 relative to each other and relative to the teeth 7. The multi-camera system 29 depicted in FIG. 1 is suitable for performing a photogrammetry method in which the object regions 17, 18, 19 and 20 are established in each of the individual images from the cameras 30 and 31, and then a three-dimensional image of the object regions 17, 18, 19 and 20 is reconstructed from the second measurement data of these established object regions.

Figure 2:
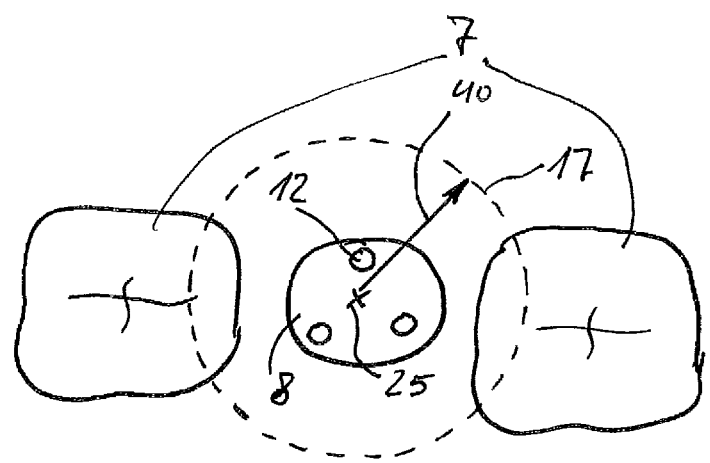
FIG. 2 shows a sketch to illustrate the automatic establishment of an object region.

FIG. 2 shows a sketch to illustrate an automatic establishment of the object region 17 between neighboring teeth 7, wherein the edge of the object region 17 is automatically established as a circle with a specific distance 40, and the axis of symmetry 25 of the implant 2 is automatically established. The distance can for example be between 4 mm and 10 mm. The position of the axis of symmetry 25 can be automatically determined by means of the measurement geometry 12 of the measured body 8.

REFERENCE CHARACTERS

1 Dental situation
2 Implant
3 Implant
4 Implant
5 Implant
6 Residual dentition
7 Teeth
8 Measured body
9 Measured body
10 Measured body
11 Measured body
12 Measurement geometry
13 Region
14 Camera
15 Overview image
16 Display device
17 Object region
18 Object region
19 Object region
20 Object region
21 Mouse cursor 22 Computer
23 Keyboard
24 Mouse
25 Axis of symmetry
26 Axis of symmetry
27 Axis of symmetry
28 Axis of symmetry
29 Multi-camera system
30 First camera
31 Second camera
32 Overall image
40 Distance/radius

The invention claimed is:

1. A method of measuring a dental situation that includes a plurality of implants and/or preparations for inserting dental restorations, comprising:
generating first measurement data of a first region of the dental situation using a first measuring method;
establishing object regions surrounding the plurality of implants and/or preparations using the first measurement data;
generating second measurement data, with a higher resolution than the first measurement data, of the established object regions using a second measuring method; and
determining respective positions and orientations of the plurality of implants and/or preparations relative to each other using the generated second measurement data of the established object regions.

2. The method according to claim 1, further comprising: combining the first measurement data and the second measurement data to create a superimposed image of the dental situation.

3. The method according to claim 1, further comprising: determining a position and an orientation of at least one of the plurality of implants and/or preparations relative to one or more teeth adjacent to an object region.

4. The method according to claim 1, wherein the object regions are established by a user.

5. The method according to claim 1, wherein the object regions are established automatically by a search algorithm.

6. The method according to claim 1, wherein the first measuring method is one of: a fringe projection method, a confocal microscopy method, a white light interferometry method, a triangulation method with colored patterns, or a three-dimensional x-ray imaging method.

7. The method according to claim 1, wherein the second measuring method is one of a triangulation method or a fringe projection method.

8. The method according to claim 7, further comprising: powdering at least one of the plurality of implants and/or preparations within the object regions prior to generating the second measurement data.

9. The method according to claim 1, wherein the first measuring method is a triangulation method with a first triangulation angle and the second measuring method is another triangulation method with a second triangulation angle that is less than the first triangulation angle.

10. The method according to claim 1, wherein the second measuring method is photogrammetry method performed by a multi-camera system.

11. The method according to claim 1, wherein the second measuring method is performed by scanning points within the object regions using a tactile scanner.

12. The method according to claim 1, wherein the second measuring method is a three-dimensional x-ray imaging method.

13. The method according to claim 1,
wherein the second measuring method is a photogrammetry method performed by a multi-camera system which produces a plurality of individual images as the second measurement data, and
wherein a three-dimensional image of the object regions is constructed from the plurality of individual images.

14. The method according to claim 1, wherein the dental situation includes the plurality of implants connected to a plurality of measuring bodies, respectively.

15. A method of measuring a dental situation that includes a plurality of implants, comprising:
generating first measurement data corresponding to an overview image of a first region of the dental situation with a camera using a first measuring method;
identifying the plurality of implants within the first measurement data corresponding to the overview image;
establishing an object region around each of the identified plurality of implants;
generating second measurement data of the established object regions, the second measurement data having a higher resolution than the first measurement data corresponding to the overview image, by use of a multi-camera system comprising a first camera and a second camera, the multi-camera system employing a second measuring method; and
determining respective positions and orientations of the plurality of implants relative to each other using the generated second measurement data of the established object regions.

16. The method according to claim 15, wherein each of the object regions extends a predetermined distance from an axis of symmetry of a corresponding implant.

17. The method according to claim 16, wherein the predetermined distance is 2 mm to 10 mm.

18. The method according to claim 15, wherein the plurality of implants within the first measurement data corresponding to the overview image are identified by use of a search algorithm.

19. A method for measuring a dental situation that includes a plurality of implants and/or preparations for inserting dental restorations, comprising:
establishing object regions surrounding the plurality of implants and/or preparations using first measurement data of a first region generated using a first measuring method; and
determining respective positions and orientations of the plurality of implants and/or preparations relative to each other using second measurement data, with a higher resolution than the first measurement data, of the established object regions, wherein the second measurement data is generated using a second measuring method.

* * * * *